US00PP35207P2

(12) United States Plant Patent
Kolster et al.

(10) Patent No.: US PP35,207 P2
(45) Date of Patent: Jun. 6, 2023

(54) ***HYDRANGEA* PLANT NAMED 'HOKOMAGRITO'**

(50) Latin Name: *Hydrangea macrophylla*
Varietal Denomination: Hokomagrito

(71) Applicants: Kolster Holding B.V., Boskoop (NL); Horteve Breeding B.V., Aalsmeer (NL)

(72) Inventors: Peter Rudolf Kolster, Boskoop (NL); Cornelis Pieter Eveleens, Aalsmeer (NL)

(73) Assignees: KOESTER HOLDING BV, Boskoop (NL), part interest; HORTEVE BREEDING BV, Aalsmeer (NL), part interest ( * ) Notice: Subject to any disclaimer, the term of this patent is extended or adjusted under 35 U.S.C. 154(b) by 0 days.

(21) Appl. No.: 18/082,935

(22) Filed: Dec. 16, 2022

(30) Foreign Application Priority Data

Sep. 27, 2022 (CA) ..... 2211079

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Hydrangea macrophylla* plant named 'Hokomagrito' that is characterized by its mophead inflorescences that are large in size and flattened in shape, its inflorescences that are white and green in color, its suitability for use as a potted plant, and its foliage that is dark green in color.

2 Drawing Sheets

Botanical classification: *Hydrangea macrophylla.*
Varietal denomination: 'Hokomagrito'.

CROSS-REFERENCE TO A RELATED APPLICATION

This application claims priority to a Canadian Plant Breeder's Rights Application No. 22-11079 filed on Sep. 27, 2022 under 35 U.S.C. 119(f), the entire contents of which is incorporated by reference herein.

BACKGROUND OF THE INVENTION

The present invention relates to a new and distinct cultivar of *Hydrangea macrophylla* and will be referred to hereafter by its cultivar name, 'Hokomagrito'. 'Hokomagrito' represents a new bigleaf *Hydrangea*, a perennial shrub grown for landscape use and as a potted plant.

'Hokomagrito' was derived from an ongoing controlled breeding program directed by the Inventors. A goal of the breeding program was to develop a new cultivar of *Hydrangea* with white and green inflorescences that performs well as a potted plant.

'Hokomagrito' arose from a controlled cross made by the Inventors in Boskoop, The Netherlands in May of 2014 between *Hydrangea* 'Qufu' as the female parent (U.S. Plant Pat. No. 26,426) and *Hydrangea* 'Napo' (U.S. Plant Pat. No. 20,614) as the male parent. 'Hokomagrito' was selected as a single unique plant from amongst the resulting seedlings in May of 2016.

Asexual propagation of the new cultivar was first accomplished by stem cuttings by one of the Inventors in July of 2016 in Boskoop, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hokomagrito' as a unique cultivar of *Hydrangea macrophylla.*

1. 'Hokomagrito' exhibits mophead inflorescences that are large in size and flattened in shape.
2. 'Hokomagrito' exhibits inflorescences that are white and green in color.
3. 'Hokomagrito' exhibits suitability for use as a potted plant.
4. 'Hokomagrito' exhibits foliage that is dark green in color.

The female parent of 'Hokomagrito' differs from 'Hokomagrito' in having inflorescences with sterile flower sepals that are pink-green in color and foliage that is lighter green in color. The male parent of 'Hokomagrito' differs from 'Hokomagrito' in having inflorescences with sterile flower sepals that are all white in color, inflorescences that are round in shape, and much longer branches. 'Hokomagrito' can be most closely compared to the *Hydrangea macrophylla* cultivars 'Hokomano' (U.S. Plant Pat. No. 22,696) and 'Hortmawin' (not patented). Both are similar to 'Hokomagrito' in having foliage that is dark green in color and inflorescences with sterile flower sepals that are white and green in color. 'Holomano' differs from 'Hokomagrito' in having mophead inflorescences that are round in shape and inflorescences with sterile flower sepal margins that are more crenate. 'Hortmawin' differs from 'Hokomagrito' in having mophead inflorescences that are more rounded in shape, inflorescences with sterile flower sepal margins that are more crenate, and mature sterile flower sepals that are more green in color.

STATEMENT REGARDING PRIOR DISCLOSURES BY THE INVENTOR

The Applicants assert that no publications or advertisements relating to sales, offers for sale, or public distribution occurred more than one year prior to the effective filing date of this application. Any information about the claimed plant would have been obtained from a direct or indirect disclosure from the Inventor. The Applicants claim a prior art exemption under 35 U.S.C. 102(b)(1) for disclosures and/or sales that fall within a one-year grace period to the effective filing date. Disclosures include website listings by Bloomin Easy Plants, NVK nurseries, and Floral Daily.

BRIEF DESCRIPTION OF THE DRAWINGS

The accompanying color photographs illustrate the overall appearance and distinct characteristics of the new *Hydrangea*. The photographs were taken of a two-year-old plant of 'Hokomagrito' as grown in a greenhouse in a 2-gallon container in Abbotsford, B.C. Canada.

The photograph in FIG. 1 provides a side view of the plant habit of 'Hokomagrito' in bloom.

Figure 1:
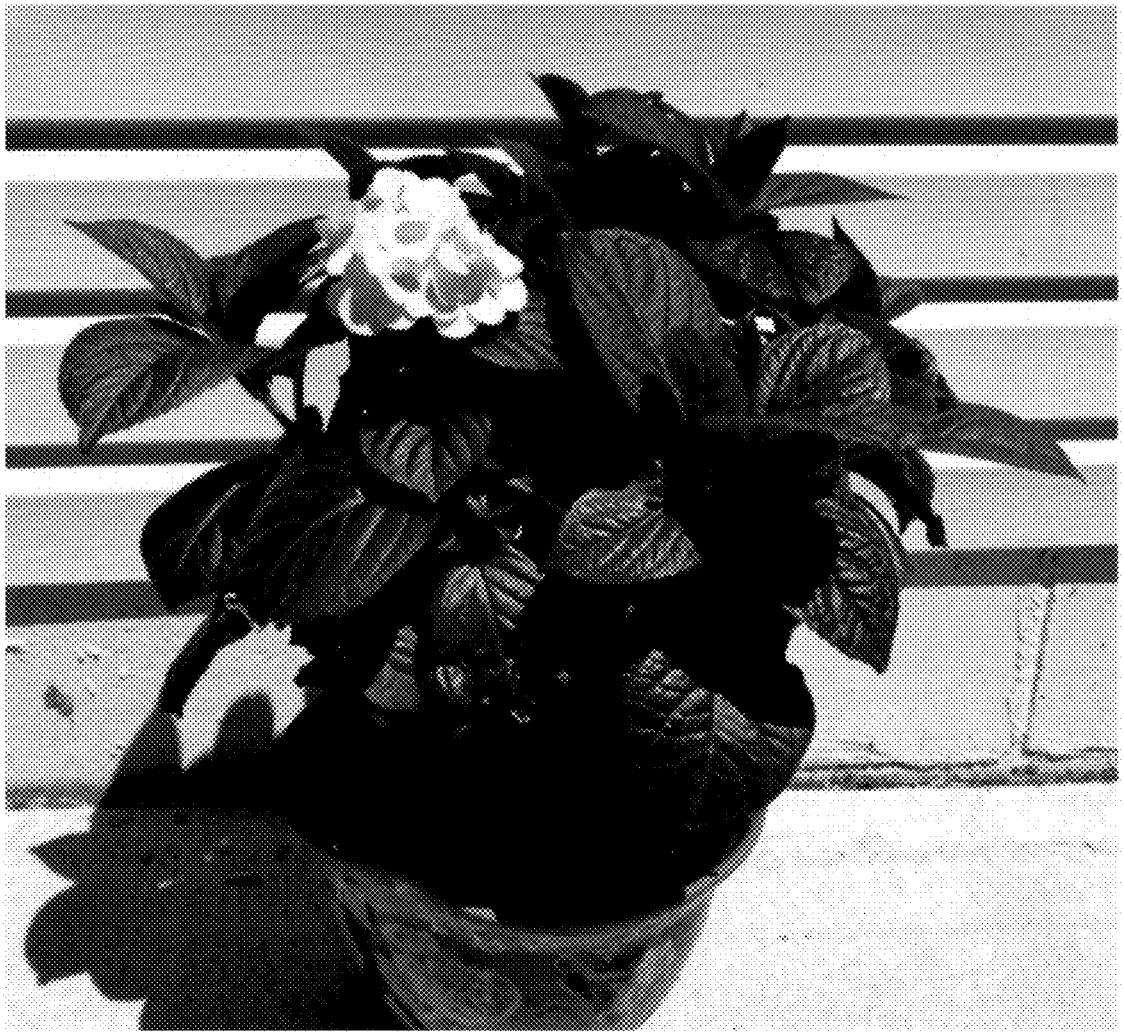
Figure 2:
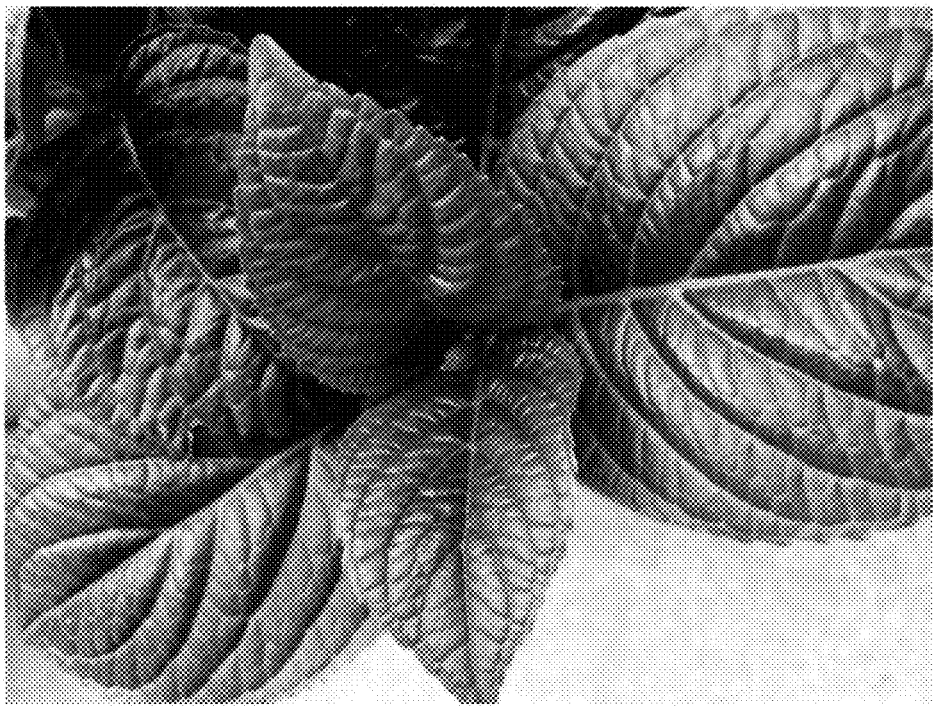

The photograph in FIG. 2 provides a close-up view of the foliage of 'Hokomagrito'.

Figure 3:
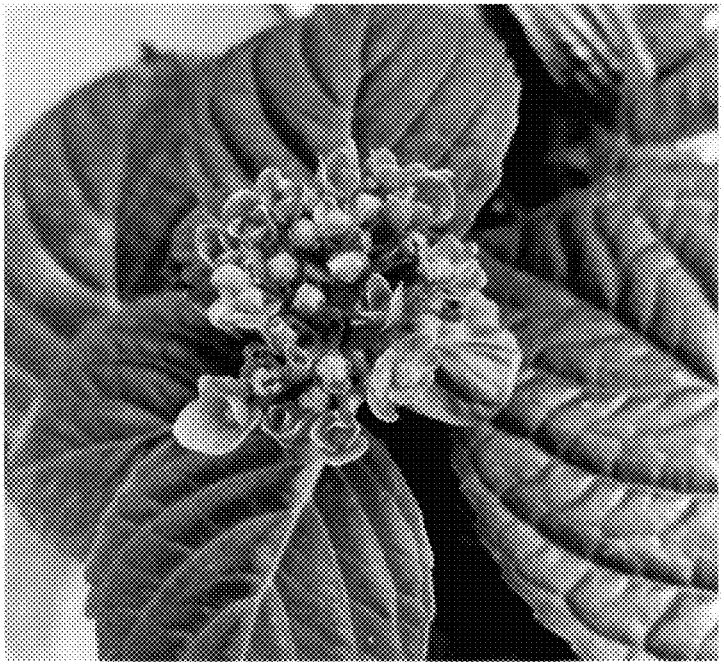

The photograph in FIG. 3 provides a close-up view of an opening inflorescence of 'Hokomagrito'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of two-year-old plants of 'Hokomagrito' as grown in a greenhouse in 2-gallon containers Abbotsford, B.C. Canada. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Late spring to late summer with flowers showy at least for 2 months in the Netherlands.

*Plant type*.—Deciduous shrub, mophead type *Hydrangea*.

*Plant habit*.—Broad spreading, upright.

*Height and spread*.—An average of 31 cm in in height and 43 cm in spread as grown in a 2-gallon container and reaches an average of 1 m in height and spread as a 3-year-old plant in the landscape.

*Hardiness*.—At least in U.S.D.A. Zones 5 to 9.

*Diseases and pests*.—No susceptibility and resistance to diseases or pests has been observed.

*Root description*.—Fine and fibrous, 161C in color.

*Propagation*.—Stem cuttings.

*Root development*.—An average of 6 weeks for root initiation with a young rooted plant produced in an average of 18 weeks.

*Growth rate and vigor*.—Moderate.

Branch description:

*Branch shape*.—Rounded.

*Branch strength*.—Strong.

*Branch color*.—Young and mature; 144B, older woody branches and bark; 200A, 200B, and 201A.

*Branch size*.—Main branches; average of 17 cm in length, 1 cm in diameter, lateral branches; an average of 15 cm in length (excluding inflorescence), 5 mm in diameter.

*Branch surface*.—Young and mature; slightly glossy, glabrous, and moderately covered with lenticels; rounded in shape, average of 18 per 1 cm diameter, average of 1 mm in length and width, 200A in color, older woody branches and bark; exfoliating, matte, dry.

*Branch aspect*.—Upright to slightly outward.

*Internode length*.—An average of 4.5 cm.

*Branching*.—Freely branching with an average of 6 main branches, 8 lateral branches per main branch.

Foliage description:

*Leaf shape*.—Broad ovate.

*Leaf arrangement*.—Opposite.

*Leaf division*.—Simple.

*Leaf base*.—Short attenuate.

*Leaf apex*.—Short apiculate.

*Leaf margins*.—Coarsely serrate.

*Leaf venation*.—Pinnate, upper vein color; veins match leaf surface color, main center vein 145B, lower vein color; 145B.

*Leaf size*.—An average of 12 cm in length and 8.5 cm in width.

*Leaf attachment*.—Petiolate.

*Leaf number*.—An average of 8 to 10 per lateral stem.

*Leaf surface*.—Upper surface; glossy, glabrous, lower surface; matte with a sheen, glabrous.

*Leaf color*.—Young and mature upper surface; 139A, young and mature lower surface; 138B.

*Petioles*.—An average of 2.2 cm in length and 4 mm in diameter, upper and lower surface color 143A, both surfaces are smooth and glossy.

Inflorescence description:

*Inflorescence type*.—Terminal panicle, flattened mophead comprised of a sterile flowers above fertile flowers.

*Lastingness of inflorescence*.—Sterile flowers; persistent for an average of 6 weeks, fertile flowers; self-cleaning, an average of 5 days.

*Inflorescence number*.—One per lateral stem.

*Inflorescence size*.—An average of 8 cm in height and 14 cm in diameter.

*Flower number*.—An average of 35 sterile flowers and 6 fertile flowers per panicle.

*Flower fragrance*.—None.

*Flower aspect*.—Upright to outward.

*Flower size*.—Sterile flowers; an average of 4 cm in diameter and 2 cm in depth, fertile flowers; do not open.

*Flower type*.—Rotate.

*Flower buds*.—Sterile and fertile flowers; an average of 2 mm in length and diameter, round and flattened in shape, 144B in color.

*Peduncles*.—Strong, flattened oval in shape, an average of 5 mm in length and 2 mm in width, 138A in color, moderately covered with lenticels; linear and thin in shape, average of 5 per 1 cm diameter, average of 0.5 mm in length and width, 200B in color, surface is glossy.

*Pedicels*.—Strong, flattened oval in shape, an average of 1 cm in length and 1 mm in width, 138A in color, moderately covered with lenticels; linear and thin in shape, average of 18 per 1 cm diameter, average of 2 mm in length, 0.5 mm in width, 200B in color, surface is glossy.

*Petals*.—Sterile flowers; petals do not open, petal spot 2 mm in diameter and 145A in color when mature, fertile flowers; do not open.

*Sepals*.—Sterile flowers; 4, rotate, broadly and bluntly acute apex with an emarginate outer tip, broadly cuneate base, entire to slightly undulate margins, reniform to nearly deltoid in shape, an average of 1.5 cm in length and 1.2 cm in width, upper and lower surface glabrous, satiny, and matte, color; when opening upper and lower surface 144B to 145A, when fully open upper and lower surface 145A, mottled with 159C, then as the sepal matures, changing to NN155D, occasionally mottled with 145A, fertile flowers; do not open.

Reproductive organs:

*Presence*.—Not observed; fertile flowers drop after budding, gynoecium and androecium not developed.

*Fruit and seed*.—Not observed.

It is claimed:

1. A new and distinct cultivar of *Hydrangea* plant named 'Hokomagrito' substantially as herein illustrated and described.

* * * * *